United States Patent
Ulmschneider et al.

(10) Patent No.: US 11,766,168 B2
(45) Date of Patent: Sep. 26, 2023

(54) ENDOSCOPE, METHOD FOR OPERATING AN ENDOSCOPE AND METHOD FOR PRODUCING AN ENDOSCOPE

(71) Applicant: KARL STORZ SE & CO. KG, Tuttlingen (DE)

(72) Inventors: Daniel Ulmschneider, Tuttlingen (DE); Christian Czupalla, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 146 days.

(21) Appl. No.: 16/885,447

(22) Filed: May 28, 2020

(65) Prior Publication Data
US 2020/0375445 A1    Dec. 3, 2020

(30) Foreign Application Priority Data

Jun. 3, 2019    (DE) .................... 10 2019 003 839.8

(51) Int. Cl.
*A61B 1/00* (2006.01)
*A61B 1/06* (2006.01)
*A61B 1/12* (2006.01)

(52) U.S. Cl.
CPC .......... *A61B 1/128* (2013.01); *A61B 1/00137* (2013.01); *A61B 1/0684* (2013.01)

(58) Field of Classification Search
CPC ... A61B 1/128; A61B 1/00137; A61B 1/0684; A61B 1/00071; A61B 1/00096;
(Continued)

(56) References Cited

U.S. PATENT DOCUMENTS

2006/0173245 A1* 8/2006 Todd ........................ A61B 1/07
600/178
2007/0060794 A1    3/2007 Efinger et al.
(Continued)

FOREIGN PATENT DOCUMENTS

DE          4313583 A1    5/1994
DE    102004045502 A1    4/2006
(Continued)

OTHER PUBLICATIONS

European Search Report for corresponding European Application No. 20175816.6, dated Jan. 19, 2021.

*Primary Examiner* — Anh Tuan T Nguyen
*Assistant Examiner* — Rynae E Boler
(74) *Attorney, Agent, or Firm* — Jason H. Vick; Sheridan Ross, PC (57) ABSTRACT

An endoscope, especially a mediastinoscope, includes an elongated shaft and a head piece situated at a proximal end section of the shaft, wherein a heat source is arranged in the head piece. At least one heat pipe extends inside the shaft, wherein a proximal end section of the at least one heat pipe is thermally coupled to the heat source and the endoscope includes an optical system which is closed by a cover glass arranged in a distal end section of the shaft. The heat source is a light source for generating an illumination radiation. The at least one heat pipe extends in the distal direction as far as the distal end section of the shaft, and at least one distal end section of the heat pipe is thermally coupled to the distal end section of the shaft.

12 Claims, 5 Drawing Sheets

(58) Field of Classification Search
CPC ....... A61B 1/00089; A61B 1/313; A61B 1/32; A61B 1/127; A61B 1/0669; A61B 1/253; A61B 1/126
USPC .......................................................... 600/175
See application file for complete search history.

(56) References Cited

U.S. PATENT DOCUMENTS

| | | | | | |
|---|---|---|---|---|---|
| 2007/0249907 | A1* | 10/2007 | Boulais | ................... | A61B 1/05 600/179 |
| 2009/0018397 | A1* | 1/2009 | Scholly | .............. | G02B 23/2476 600/178 |
| 2011/0144436 | A1* | 6/2011 | Nearman | ................ | A61B 1/267 600/188 |
| 2011/0306834 | A1* | 12/2011 | Schrader | .................. | A61B 1/12 600/112 |
| 2012/0034573 | A1* | 2/2012 | Erdmann | .............. | A61B 1/0008 433/29 |
| 2013/0310644 | A1* | 11/2013 | Ichimura | ................ | A61B 1/051 600/109 |
| 2014/0316194 | A1* | 10/2014 | Rapp | ....................... | A61B 1/018 600/104 |
| 2015/0335233 | A1* | 11/2015 | Pilz | .................... | A61B 1/00128 600/101 |
| 2016/0030707 | A1* | 2/2016 | Dillon | .................... | A61B 1/012 600/156 |

FOREIGN PATENT DOCUMENTS

| | | |
|---|---|---|
| DE | 102007032200 A1 | 1/2009 |
| DE | 102014107205 A1 | 11/2015 |
| EP | 2394567 A1 | 12/2011 |
| EP | 2792292 A1 | 10/2014 |
| EP | 2888992 A1 | 7/2015 |
| EP | 2946718 A1 | 11/2015 |

* cited by examiner

ENDOSCOPE, METHOD FOR OPERATING AN ENDOSCOPE AND METHOD FOR PRODUCING AN ENDOSCOPE

CROSS REFERENCE TO RELATED APPLICATIONS

This application claims the benefit under 35 U.S.C. 119(a) to German Patent Application No. 10 2019 003 839.8, filed Jun. 3, 2019, the disclosure of which is incorporated herein by reference in its entirety.

SUMMARY

The present technology relates to an endoscope, especially a mediastinoscope, as well as a method for operating an endoscope and a method for producing a corresponding endoscope.

Endoscopes for medical or technical applications comprise an elongated shaft designed to be introduced into a cavity, containing optical and/or electronic components for taking a picture of a scene in the cavity and for relaying the picture to a display or viewing device located outside the cavity. In order to adequately illuminate the endoscopic scene being photographed, it is known how to conduct illuminating light generated by an external illumination device through a fiber optical cable to the endoscope, or how to arrange one or more light sources inside the endoscope, such as light-emitting diodes (LEDs). Yet this results in heat loss during the operation, leading to a heating of the endoscope. Moreover, an endoscope may have further heat sources, such as an electronic image sensor to take an endoscopic picture and electronic circuits for evaluation the image data so produced.

Such heat sources may be arranged in the distal (i.e., away from the user) or in the proximal (i.e., near the user) end section of the endoscope or in a handle, causing a temperature rise there. But as a rule, an excessive heating is also undesirable in partial regions of the endoscope surface, especially in the case of endoscopes for medical applications. Thus, a heating of the surface of the shaft above a temperature of 41° C. may result in injury to bodily tissue coming into contact with the endoscope. Likewise, an excessive heating of the handle may interfere with the use of the endoscope. It is therefore desirable to dissipate or distribute the heat loss generated by the heat sources.

In DE 10 2007 032 200 A1 there is disclosed an endoscope having a handle as well as a probe piece which can be connected to it, wherein an illumination system with at least one light-emitting diode is arranged in the handle. For the at least one light-emitting diode, a support element made of heat-conducting material is arranged inside the handle, with which the light-emitting diode is directly connected and which can be in thermal contact with housing parts and/or installed parts of the handle and the probe piece.

According to EP 2 394 567 A1, an endoscope comprises an elongated shaft, a head piece at a proximal end of the shaft, a light source arranged in the shaft in a distal region thereof, which generates heat loss, and a passive cooling in the form of a heat pipe arranged in the shaft, which is thermally coupled to the light source, in order to dissipate the heat loss in the proximal direction. The heat pipe extends into the head piece of the endoscope, where a heat sink body is located with which the heat pipe is thermally coupled and which takes up the heat loss from the heat pipe and gives it off to the surroundings, directly or through a housing of the head piece.

From EP 2 946 718 A1 there is known an endoscope, comprising an elongated tubular shaft, a heat source generating heat loss, and a heat pipe, extending in the interior of the shaft in the longitudinal direction of the shaft and being thermally coupled to the heat source, in order to take up heat from it and carry it away from the heat source. The heat pipe is coupled flush with the shaft in thermal conduction between its distal and its proximal end along at least a partial length of the heat pipe and at least a partial circumference of the heat pipe, in order to dissipate heat from the heat pipe to the surroundings along at least a partial length and at least a partial circumference of the shaft.

In DE 10 2014 107 205 A1 there is disclosed an optical medical instrument, especially an endoscope or exoscope, comprising an elongated tubular shaft, a heat source generating heat loss, and a heat pipe, which extends in the interior of the shaft in the longitudinal direction of the shaft and comprises a distal heat pipe end and a proximal heat pipe end, wherein the heat pipe is thermally coupled to the heat source in order to take up heat from it and carry it away from the heat source.

DE 10 2004 045 502 A1 relates to an expandable medical instrument for endoscopic procedures having a base body, a handle arranged in the base body, and at least two spatula blades connected to the handle, which can be adjusted by an adjusting mechanism between a starting closed position and at least one working position, parallel and/or slanted with respect to each other.

However, it has been discovered that the heat loss generated in the aforementioned endoscopes, especially in a proximal end region of the endoscope, is not always optimally dissipated or distributed within the endoscope. Thus, the dissipation and distribution of the heat loss which occurs in the aforementioned endoscopes may result in a temperature distribution across the surface of the endoscope which is not optimal, especially in an initial phase of the endoscopic procedure, when the endoscope is still cold, i.e., for the most part has the ambient temperature.

The problem which the present invention proposes to solve is to indicate an improved endoscope, especially an improved mediastinoscope, wherein the endoscope or the mediastinoscope is improved especially in regard to its heat management. Further, a problem which the present technology proposes to solve is to indicate a corresponding method for operating an endoscope and a method for producing such an endoscope.

This problem is solved by an endoscope according to the claims as appended hereto, by a method for operating an endoscope, and by a method for producing an endoscope.

Advantageous embodiments of the technology will emerge from the dependent claims.

An endoscope according to the technology is preferably a medical endoscope, especially a mediastinoscope; but the endoscope may also be, for example, a laryngoscope or an endoscope or endoscopic instrument suitable for other applications. Preferably, the endoscope is a video endoscope, and especially preferably a video mediastinoscope.

An endoscope according to the technology comprises an elongated shaft, designed in particular for introduction into an internal cavity of a human or animal body through a natural or an artificially created bodily opening. The shaft preferably has a rigid design and may comprise an outer shaft, which may be formed for example as an approximately cylindrical tube or in the shape of a spatula. Moreover, the endoscope comprises a head piece situated at a proximal end section of the shaft. The head piece may be fashioned for example as a handle or part of a handle, or it may be designed to secure a handle or part of a handle; the head piece may on the other hand be a proximal end section of the shaft. Preferably, the head piece stands off from the shaft transversely to a longitudinal direction of the shaft. In the head piece there is arranged at least one heat source, which gives off heat loss during the operation of the endoscope.

Inside the shaft there extends at least one heat pipe, substantially in a longitudinal direction of the shaft, while a proximal end section of the at least one heat pipe is thermally coupled to the heat source. Here "thermal coupling" means a direct contact, such as a flush contact, or a connection by way of a heat-conducting material or one or more components made of heat-conducting materials, wherein the contact or the connection is suitable for heat transfer. Options for heat-conducting materials are, in particular, metallic materials or perhaps heat-conducting paste or thermal adhesive. In the present context, this type of heat-conducting connection, called thermal coupling, is in particular a connection along a length which is significantly shorter than the length of the shaft or shorter than a diameter of the shaft of the endoscope. Thus, when a temperature gradient is present, a heat transport will occur via the thermal coupling. The heat pipe is thermally coupled to the heat source in particular to carry away the heat loss of the heat source and to transfer at least a portion of the heat loss to the shaft in the distal direction. The heat pipe can also be called a "heatpipe."

Further, the endoscope comprises an optical system for taking a picture of an object field in the cavity, such that the system is closed at the object end by a cover glass and situated in a distal end section of the shaft. The optical system can be arranged within the distal end section of the shaft and it may comprise, for example, a lens and an electronic image sensor connected to the lens, but it may also extend within the shaft into the proximal end section of the shaft. In particular, the optical system extends in parallel with a lengthwise axis of the shaft. The cover glass preferably has a flat surface, at least at the object end, which may stand perpendicular, at a slant, or parallel to the lengthwise axis of the shaft, depending on the viewing direction of the endoscope and the configuration of the lens. The cover glass closes off the optical system, especially at the distal end, and it may for example form part of a distal end face of the endoscope or be set back in the proximal direction from a distal end of the shaft.

According to the technology, the heat source arranged in the head piece of the endoscope is at least one light source for generating an illumination radiation, which can be conducted in the cavity for example through light guides extending inside the shaft as far as the distal end section of the shaft, in order to illuminate the cavity or the object field. Further, according to the technology, at least one heat pipe extends in the distal direction as far as the distal end section of the shaft and thus at least approximately up to the level of the cover glass. At least one distal end section of the heat pipe is thermally coupled to the distal end section of the shaft. In particular, the distal end or the distal end section of the heat pipe is thermally coupled to the outer shaft, in which the cover glass can be embedded or by which the cover glass can be at least partly enclosed. Due to the thermal coupling, a heat transfer occurs, especially transversely to the longitudinal direction of the shaft.

It has been discovered according to the technology that heat loss of the at least one light source which is created during the operation of the endoscope can be utilized in order to heat specific surface regions of the endoscope for which a higher temperature is advantageous. This applies in particular to surface regions in the distal end section of the shaft, such as a surface of the distal end section of the outer shaft, and for the cover glass of the optical system. The heat management according to the technology is thus designed not only to carry away heat loss, but also to distribute it and utilize it in a targeted manner for heating surface regions.

Due to the facts that the heat source is a light source for generating the illumination radiation, that the heat pipe extends into the distal end section of the shaft, and that at least one distal end section of the heat pipe is thermally coupled to the distal end section of the shaft, the heat loss of the light source created during the operation of the endoscope can be utilized specifically to heat the distal end section of the shaft of the endoscope. In this way, especially when the distal end section of the heat pipe is thermally coupled to the outer shaft, a targeted heating of the surface of the distal end section of the shaft of the endoscope is made possible. It is thus possible to first heat the portion of the shaft of the endoscope that first comes into contact with the bodily tissue of a patient after the endoscope is placed in operation, so that the endoscope already has a surface temperature close to the body temperature of the patient when, for example, it is introduced into the bodily opening.

Moreover, due to the fact that the heat pipe which is connected by thermal conduction to the at least one light source in order to carry away the heat loss is thermally coupled to the shaft in a portion of the shaft in which the cover glass of the optical system of the endoscope is situated, it is possible, by means of the heat loss given off by the light source, to at least slightly heat the cover glass closing off the optical system at the object end. This is especially advantageous in the initial phase of an endoscopic procedure, since the shaft of the endoscope is often much cooler when introduced into an internal cavity of the body than the temperature prevailing in the cavity, so that the moisture present in the cavity may become deposited on the cover glass and impair the endoscopic view. In this way, it is possible to prevent a fogging of the cover glass and to improve the endoscopic view.

Preferably, the optical system is received in an optical shaft extending in the shaft of the endoscope parallel to the lengthwise axis of the shaft, and the distal end section of the optical shaft is thermally coupled to the distal end section of the shaft, especially to the outer shaft. The optical shaft may be joined firmly to the shaft of the endoscope, or it may be inserted therein and be coupled thermally to it by soldering or with thermal adhesive, at least for a portion. The optical shaft may be closed off distally by the cover glass. The optical shaft may be hermetically sealed, with the optical shaft able to be formed by an approximately cylindrical tube in whose distal end the cover glass is hermetically sealed. Moreover, an electronic image sensor may be contained in the optical shaft, which may likewise be arranged in particular in the distal end section of the optical shaft, while the optical system comprises an endoscope lens, which produces an image of the object field on a sensor surface of the image sensor. Because of the fact that the at least one heat pipe reaches into the region of the lens and the cover glass, it is possible to achieve an adequate heat transfer to the distal end section of the optical shaft and thus to the cover glass in an advantageous manner. The heat transfer can be further improved in that the optical shaft, at least in its distal end section, is thermally coupled to the shaft or to the outer shaft, with the heat transfer likewise occurring substantially transversely to the longitudinal direction of the shaft.

It may be provided preferably that the at least one heat pipe is additionally thermally coupled to the shaft in a middle section, such as over a portion of its length or over substantially its entire length within the shaft. In particular, the heat pipe may be thermally coupled to the outer shaft in its middle section and be thermally coupled to the at least one heat pipe running within the shaft at least along a portion of the length of the outer shaft, for example half or three quarters of the length of the outer shaft. The outer shaft is preferably designed to be highly thermally conductive, for example, being made of a metallic material. In this way, a large or predominant portion or almost the entire outer surface of the shaft can be utilized to carry away the heat loss generated by the light source, and in particular the outer shaft may serve as a heat sink body. In this way, in addition to the targeted heating of the distal end section of the shaft, an efficient heat dissipation can also be achieved. Moreover, it can be more securely prevented in this way that a surface of the shaft having a higher than the maximum allowable temperature will come into contact with the bodily tissue of the patient.

According to an especially preferred embodiment of the technology, the shaft comprises an outer shaft having an overhanging section extending in the distal direction beyond the cover glass, wherein the at least one heat pipe extends in the distal direction only as far as the cover glass or approximately as far as the cover glass. In particular, it may be provided that the at least one heat pipe extends in the distal direction only or approximately only to the level of the lens or an electronic image sensor located in the distal end section of the optical shaft. The outer shaft can for example be designed as a tube or a spatula. According to one especially advantageous embodiment, the endoscope is designed as a mediastinoscope, wherein the shaft is formed by a lengthwise slotted tube having a thickening on the inside extending in the longitudinal direction in which the optical shaft is embedded. At the distal end, the shaft has a beveled section protruding beyond the distal end of the optical shaft in the distal direction, thereby creating a working space when the mediastinoscope is in use, within which manipulations can be performed under endoscopic viewing, for example the removal of a biopsy. Due to the fact that the outer shaft comprises this kind of overhanging section extending distally beyond the cover glass, into which the at least one heat pipe does not reach, a design is created in which a heating of the cover glass is made possible, since this constitutes the warmest surface region within the working space. In this way, the cover glass can be prevented from becoming fogged up in an especially reliable manner.

According to another aspect of the technology, which can also be claimed independently of the previously described aspects, the at least one heat pipe is inserted into a blind bore extending in the shaft from the proximal direction. In particular, the blind bore is introduced from the proximal direction into an outer shaft of the endoscope and closed at the distal end. According to this aspect of the technology, the blind bore is furthermore connected near its distal end by a transverse bore to an additional bore of the shaft extending in the longitudinal direction of the shaft, and the at least one heat pipe is embedded in thermal adhesive in the blind bore. Due to the fact that the at least one heat pipe is installed in a blind bore, so that an especially large surface is available for the heat transfer, and due to the fact that the at least one heat pipe is thermally coupled by means of thermal adhesive to the shaft, especially to the outer shaft, a thermal coupling which is adequate in many instances can be achieved for the transfer of at least a portion of the heat loss of the light source to the shaft or the outer shaft. The heat transfer can be further improved if the at least one heat pipe is installed with narrow tolerances in the blind bore. Because the blind bore is connected near its distal end by a transverse bore to the additional lengthwise bore, it can furthermore be achieved that excess thermal adhesive can escape through the transverse bore from the distal region of the blind bore, so that a build-up of back pressure can be avoided, which would hinder the further introduction of the heat pipe into the blind bore. In this way, the manufacturing of the endoscope can be made easier.

It is furthermore preferable for the additional lengthwise bore to be formed as a through bore of the shaft, especially the outer shaft, which extends in the longitudinal direction of the shaft and in which the optical system is contained, or in which the optical shaft is installed. In this way, both a simple construction and an easy installation and at the same time an especially efficient thermal coupling of the at least one heat pipe to the shaft can be achieved.

In an especially advantageous manner, it may be provided that the at least one blind bore, the at least one transverse bore and the additional lengthwise bore are accommodated in an outer shaft of the shaft, wherein the outer shaft is formed as a single piece, preferably made of a metallic material, such as stainless steel. The outer shaft may be tubular or spatula-shaped, for example. Thanks to the single-piece design, the heat transfer can be further improved. Such a single-piece outer shaft made of metallic material can be produced, for example, by laser sintering.

Preferably, the endoscope comprises two heat pipes arranged on either side of the optical system or the optical shaft, especially symmetrically to the optical shaft, and running at least for a section in parallel with the optical system or the optical shaft. In this way, a further improved heat transfer to the shaft or to the outer shaft and to the cover glass can be achieved.

It is furthermore preferable for the light source to be formed by at least one light-emitting diode (LED) and one LED support on which the at least one LED is secured, wherein the at least one heat pipe is thermally coupled to the LED support. In a further preferred manner, a light guide is optically coupled to the at least one LED, extending through the shaft as far as its distal end section and designed to conduct the illumination radiation produced by the light source to an object field being observed. The at least one LED can be encased together with the proximal end of the light guide in a casting compound in order to prevent moisture from getting into the light source, at least for the most part. The at least one LED may be arranged transversely to the longitudinal direction of the shaft.

According to another aspect of the technology, which can also be claimed independently of the previously-described aspects, the endoscope comprises a handle with a housing wherein is received an electronics unit having a shell which lies flush with or interlocking against an inner side of the housing. The handle may be formed entirely or partially by the head piece of the shaft or be joined to the head piece of the shaft, in particular the housing of the handle may be mounted on the head piece. For example, the handle may be angled by 90° with respect to the longitudinal direction of the shaft. The electronics unit comprises in particular electrical and electronic circuits for the power supply and control of the light source and/or for the power supply and control of an electronic image sensor and/or for the image processing or image preprocessing of the image signals furnished by the electronic image sensor. The shell of the electronics unit may be hermetically sealed. Thanks to the mounting of the electronics unit in the handle, a better space utilization is advantageously achieved, so that a more compact design of the endoscope is made possible. Furthermore, the handle basically enlarges the outer surface of the head piece, so that a quicker or more efficient heat dissipation is made possible.

According to this aspect of the technology, the endoscope thus comprises at least two heat sources, namely, the light source and the electronics unit, and for the dissipation of the heat loss produced by the respective heat source there are provided two corresponding heat sinks with respective, separate heat paths. The heat loss given off by the electronics unit is efficiently transferred by the flush arrangement of the shell of the electronics unit against the housing of the handle and from this to the surroundings. The flush arrangement of the shell can be provided by appropriately machined heat exchange surfaces of the shell and the housing. A further improvement in the heat transfer can be achieved by thermal paste.

The electronics unit may in particular comprise a board mounted with electronic circuits as well as a metallic support, wherein the board and the support can be thermally coupled to the shell of the electronics unit by means of thermal paste or thermal adhesive, in particular the board can be thermally coupled to the support, and the support to the shell. In this way, a further improved dissipation of the heat loss generated by the electronics unit can be made possible.

In a method according to the technology for operating an endoscope, especially a mediastinoscope, whereby the endoscope comprises an elongated shaft and a head piece situated at a proximal end section of the shaft, a light source arranged in the head piece is placed in operation, at least a portion of the lost heat generated by the light source is conducted into the distal end section of the shaft by at least one heat pipe whose proximal end section is thermally coupled to the light source and extends inside the shaft. This enables the heat loss from the light source to be used in a simple manner for warming the distal end section of the shaft, whereby in particular a surface of the distal end section of an outer shaft of the endoscope and/or a cover glass closing off an optical system of the endoscope at the lens side can be heated. This is advantageous in particular at the beginning of an endoscopy procedure. The endoscope is in particular designed as described above and is especially preferably a video mediastinoscope.

In an especially advantageous manner, it may be provided that the light source is already placed in operation for a period of time prior to the use of the endoscope in order to achieve an optimal temperature distribution of the surface of the endoscope already at the beginning of the procedure.

In a method according to the technology for producing an endoscope, an outer shaft of the endoscope is prepared which comprises at least one blind bore reaching into the outer shaft from the proximal direction, an additional lengthwise bore, and a transverse bore which joins the blind bore near its distal end to the lengthwise bore. The blind bore is filled at least partly with thermal adhesive. A heat pipe is then inserted into the blind bore from the proximal direction, the thermal adhesive escaping through the transverse bore into the lengthwise bore. An optical shaft is inserted into the lengthwise bore, whereby excess thermal adhesive can be removed from the lengthwise bore. The method may involve further steps. In particular, the endoscope can be configured as described above.

In an especially preferred manner, the outer shaft containing the at least one blind bore, the transverse bore and the additional lengthwise bore is formed as a single piece and is produced in particular by means of a laser sintering method.

Of course, the features mentioned above and those yet to be explained in the following can be used not only in the particular indicated combination, but also in other combinations or standing alone, without departing from the scope of the present technology.

BRIEF DESCRIPTION OF THE DRAWINGS

Further aspects of the technology will emerge from the following description of a preferred exemplary embodiment and the accompanying drawing.

DETAILED DESCRIPTION

Figure 1:
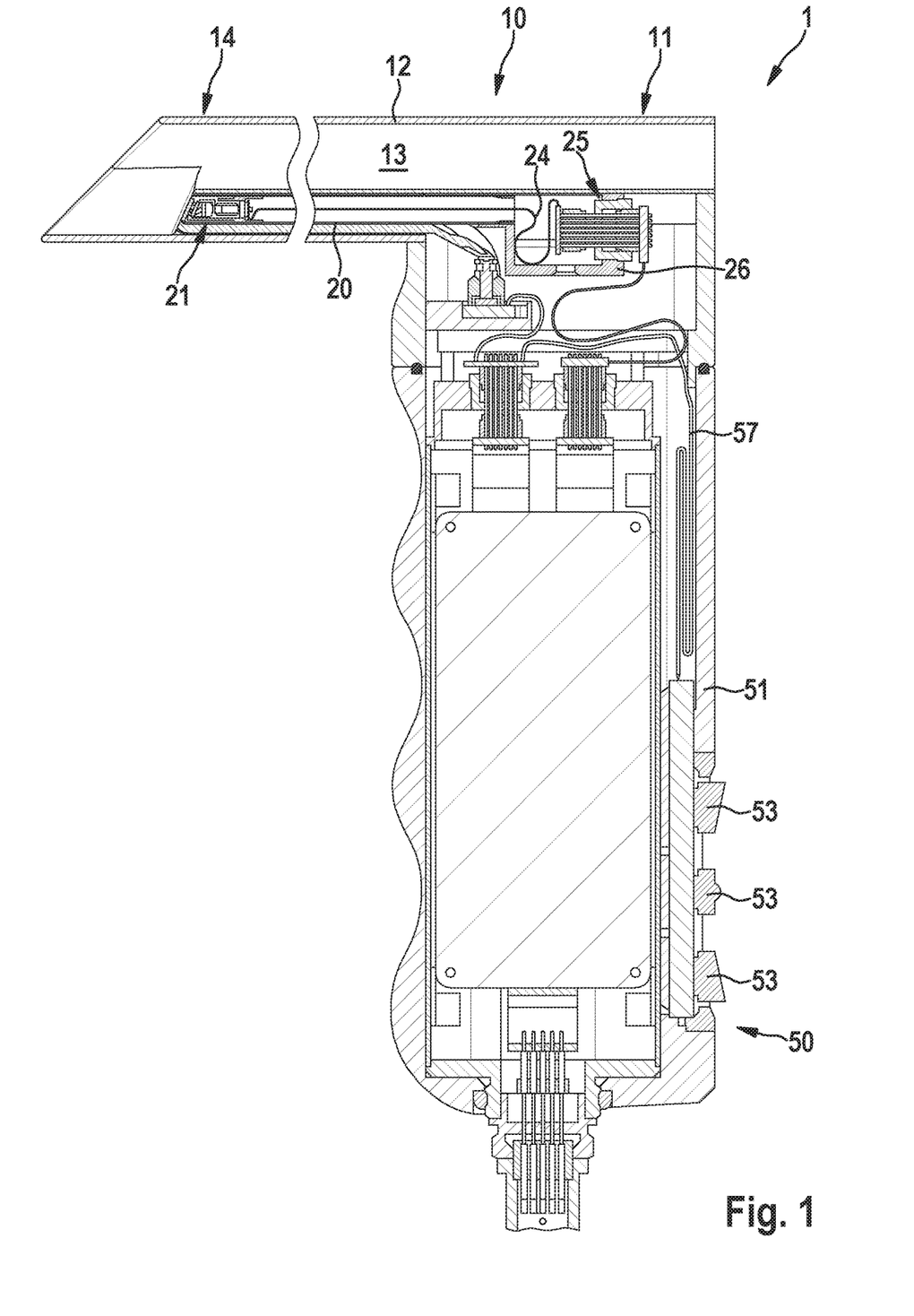
FIG. 1 shows an exemplary embodiment of an endoscope according to the technology in a longitudinal section.
Figure 2:
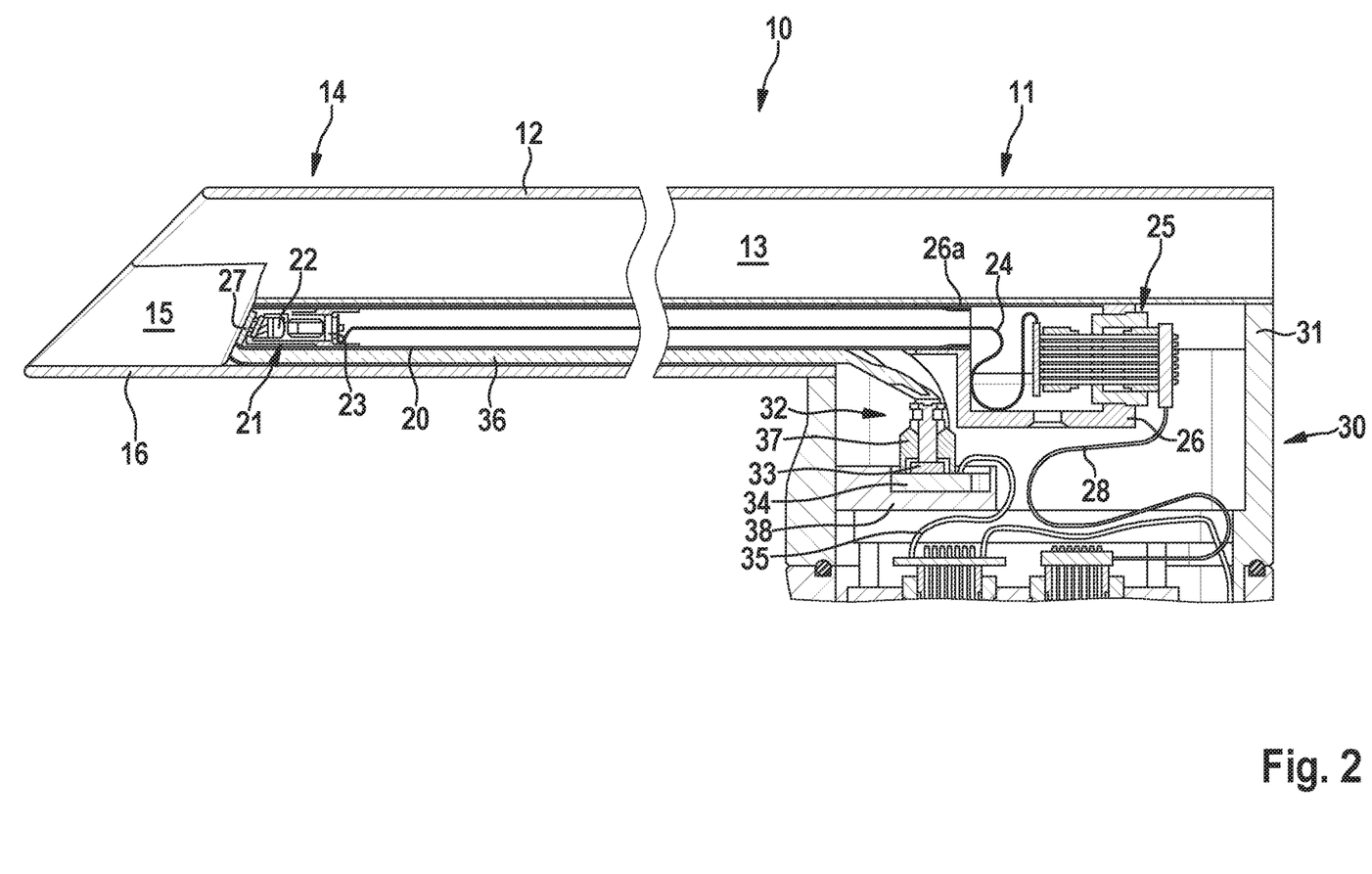
FIG. 2 shows a magnified longitudinal section of the shaft and the head piece of the endoscope of FIG. 1.

FIG. 1 shows an endoscope according to one exemplary embodiment of the present technology in a longitudinal cross section view, and FIG. 2 shows it in a magnified longitudinal section view of the shaft and the head piece, wherein the sectioning plane of the endoscope is vertical and corresponding approximately to a midplane of the shaft and the handle. Here and in the following, the position and direction statements pertain to the position of the endoscope as shown in FIG. 1. In the exemplary embodiment shown, the endoscope is a mediastinoscope, especially a video mediastinoscope. However, the technology is not limited to this, but instead an endoscope according to the technology may be designed accordingly as a laryngoscope or for other endoscopic applications.

As is shown in FIG. 1, the mediastinoscope 1 comprises an elongated shaft 10, which is designed to be introduced through an incision into the mediastinum, as well as a handle 50. The shaft may in particular have a length of around 10-40 cm, for example around 20 cm. The handle 50 is arranged on a proximal end section 11 of the shaft 10 and protrudes downward from the shaft 10 approximately at a right angle in relation to the position of the mediastinoscope 1 shown in FIG. 1. The shaft 10 comprises an outer shaft, which in the exemplary embodiment shown is formed by an approximately cylindrical tube 12 which has a slot passing through it in the longitudinal direction. The tube 12 constitutes the spatula of the mediastinoscope 1 and consists for example of stainless steel. The tube 12 encloses a continuous cavity 13 in the longitudinal direction through which instruments can be moved, for example to take biopsies. In the distal end section 14 of the shaft 10, which is opposite the proximal end section 11, the cavity 13 leads to a working space 15.

In the lower region of the tube 12, a thickening is located on the inside, having a lengthwise bore in which an optical shaft 20 is installed which is firmly joined to the tube 12, for example by soldering or gluing with thermal adhesive. Inside the optical shaft 20 there is received an imaging unit 21 comprising a lens 22 and an electronic image sensor 23. The electronic image sensor 23 may be a CCD or MOSFET sensor, for example. The image signals generated by the electronic image sensor 23 are taken via a flex board 24 to an electrical connector 25 at the proximal end of the optical shaft 20. Further details on the arrangement and the electrical connections of the electronic image sensor 23 are described in the German patent application of the same applicant, filed on the same date as the present application, entitled "Endoscope and method for manufacturing an endoscope" (our reference: KST082), which is incorporated here in the present application by reference.

Together with a proximal connector housing 26, the optical shaft 20 forms a hermetically sealed space. For this, the connector 25 is installed in a hermetically tight manner in the connector housing 26 and the distal end of the optical shaft is closed off by the likewise hermetically sealed cover glass 27. Further details on the hermetically sealed configuration of the optical shaft 20 together with the connector housing 26 are described in the German patent application of the same applicant, filed on the same date as the present application, entitled "Video endoscope" (our reference: KST083), which is incorporated here in the present application by reference.

The tube 12 of the shaft 10 is distally beveled and forms an overhanging section 16 extending beyond the optical shaft and beyond the position of the cover glass 27 in the distal direction. The overhanging section 16 of the tube 12 encloses the working space 15, which can be used for surgical manipulations under endoscopic viewing. For this, the lens 22 is configured for a viewing direction slanted to the longitudinal direction of the shaft 10 and the cover glass 27 is slanted accordingly.

Further, it is shown in FIG. 1 and FIG. 2 that a head piece 30 is mounted at the proximal end section 11 of the shaft 10, comprising a head piece housing 31 in which the connector housing 26 and a light source 32 are contained. Moreover, electrical connection cables are contained in the head piece housing 31 (see below). The light source 32 comprises a LED 33, which is mounted on a carrier plate 34 and makes contact there with electrical cables 35. The LED 33 is optically coupled to a light guide 36, which is formed by a strand of optical fiber, and which relays the illumination light generated by the LED 33 to the distal end section 14 of the shaft 10, where it emerges from the optical fibers to illuminate an object field or the working space 15. The optical fiber strand is held in a light guide socket 37. The carrier plate 34 is secured to a metallic support 38, which is mounted on the inside of the head piece housing 31.

Figure 3:
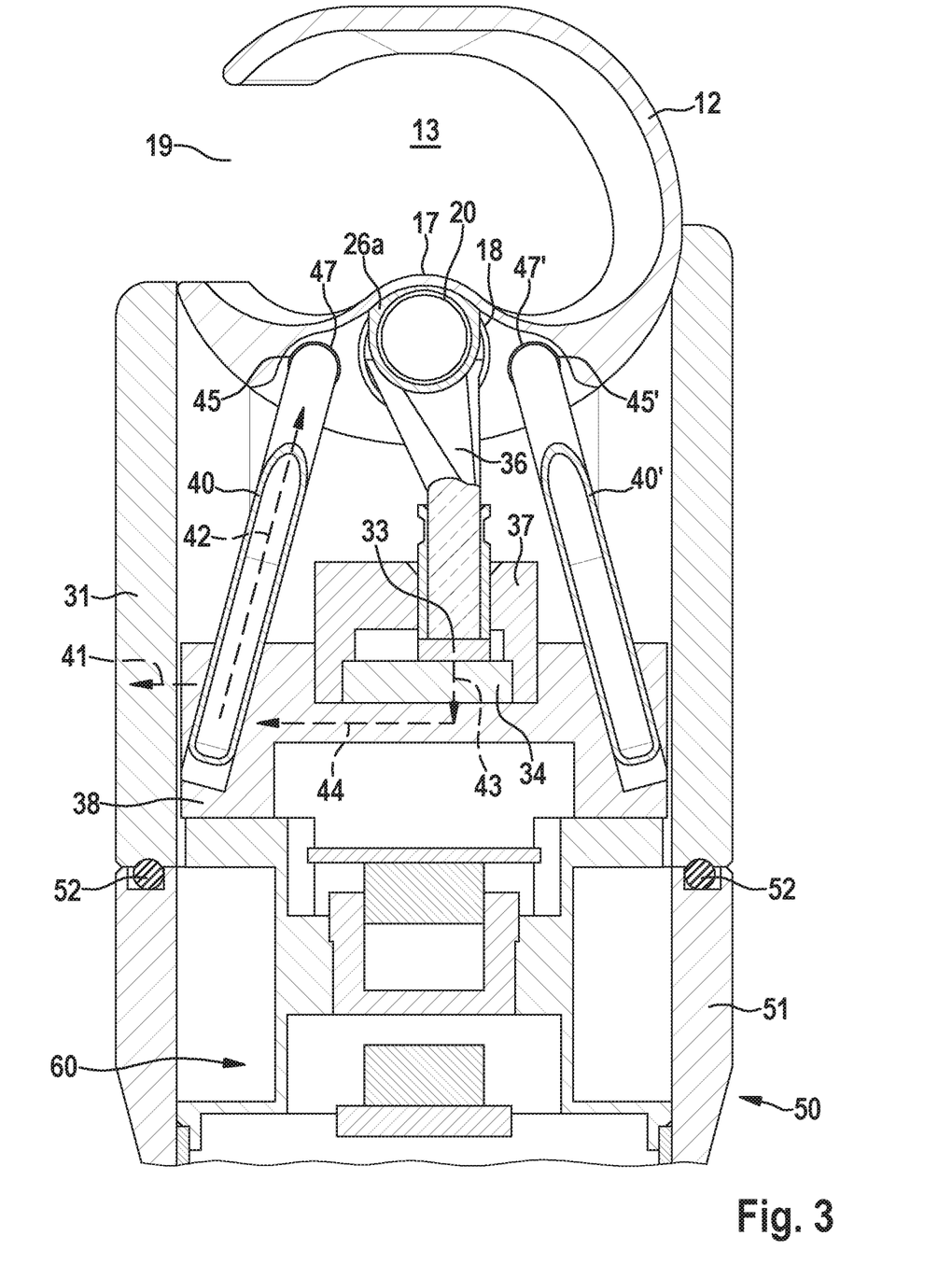
FIG. 3 shows a transverse section through the shaft and the head piece of the endoscope of FIG. 1.

FIG. 3 shows a transverse section through the shaft 10 and through the head piece 30 in the region of the LED 33, looking from the proximal direction. As is shown in FIG. 3, the LED 33 is optically coupled to the light guide 36, with the proximal end of the optical fiber strand forming the light guide 36 being held in the light guide socket 37. The light guide 36 runs beneath and to the side of the optical shaft 20 further in the distal direction through the tube 12 of the shaft 10. Furthermore, it is shown in FIG. 3 that the LED 33 is mounted on the LED carrier plate 34, which is secured to the support 38 and joined to it in a thermally conductive manner, for example by lying against it with its entire surface. Two heat pipes (40, 40') are installed in bores of the support 38 and are coupled thermally by means of thermal adhesive to the support 38. As indicated in FIG. 3 by the arrows 41, 42, the heat loss arising during the operation of the LED 33 and taken via the LED plate 34 to the support 38 is injected in a small portion directly into the head piece housing 31 (arrow 41) and in a larger portion dissipated by means of the heat pipe 40, 40' (arrow 42). The heat flux from the LED 33 through the LED plate 34 and inside the metallic support 38 is indicated by the arrows 43, 44.

As is likewise indicated in FIG. 3, the tube 12 of the shaft 10 is approximately cylindrical in shape, but it is flattened at the top in its proximal end section 11. In the lower region of the tube 12, the tube has a thickening, which extends as an interior bulge 17 in the longitudinal direction of the tube 12. There are formed in the bulge 17 a continuous central lengthwise bore 18 and two blind bores 45, 45' running laterally and parallel to this in which the heat pipes 40, 40' are situated, each of which is embedded in thermal adhesive 47, 47' and coupled thermally to the tube 12. The optical shaft 20 and the light guide 36 run in the lengthwise bore 18. Furthermore, it is shown in FIG. 3 that a housing 51 of the handle 50 is mounted by means of a seal 52 on the head piece housing 31. An electronics unit 60 is contained inside the housing 51 (see below).

Figure 4:
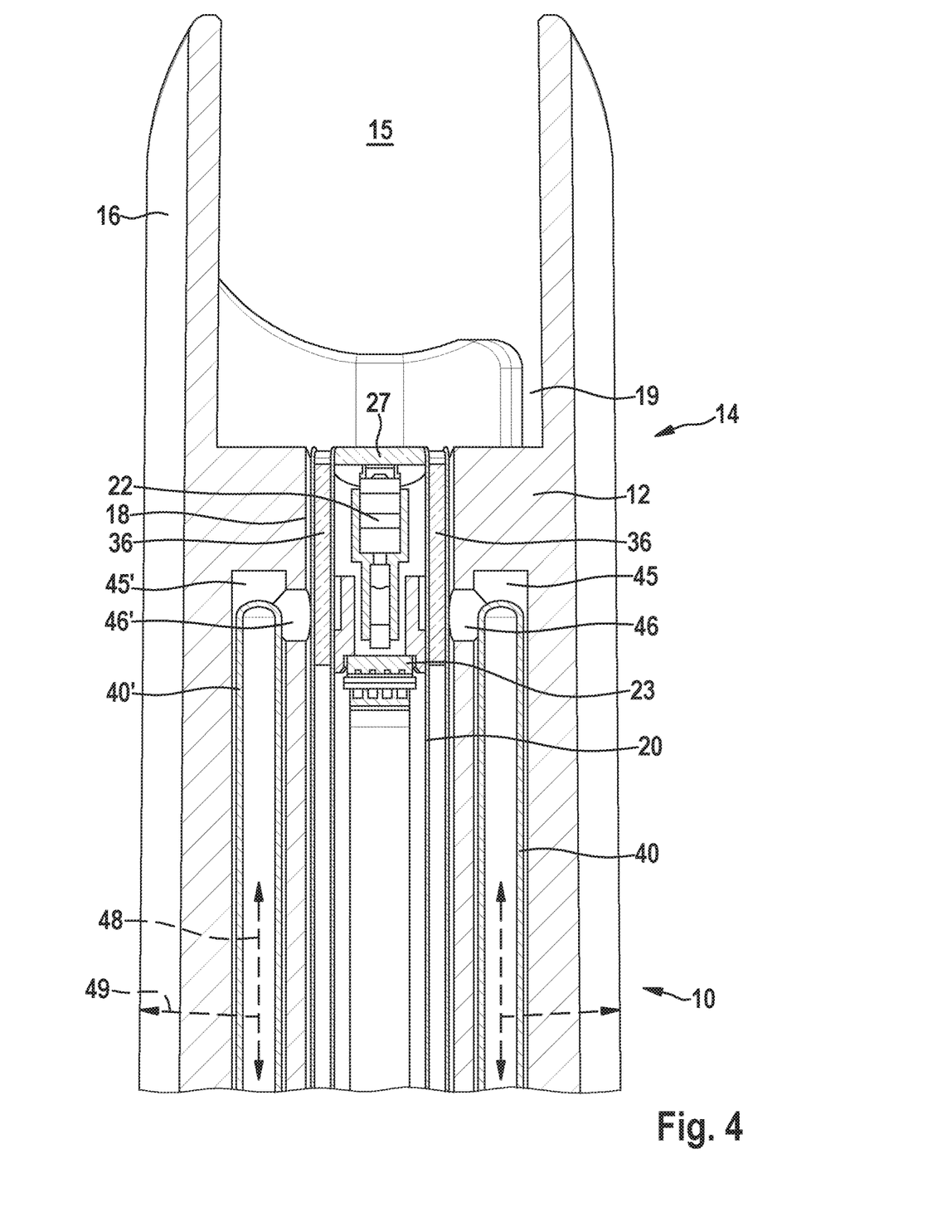
FIG. 4 shows a longitudinal section through the distal end section of the shaft of the endoscope of FIG. 1 with a horizontal sectioning plane.

As shown in the horizontal longitudinal section through the distal end section 14 of the shaft 10 represented in FIG. 4, the blind bores 45, 45' end in the distal direction shortly before the distal end of the optical tube 20. The optical tube 20, in whose distal end section the lens 22 and the electronic image sensor 23 are situated, is hermetically sealed by the cover glass 27. The distal end section of the light guide 36 is indicated at the side of the optical tube 20. Near the distal end of the blind bores 45, 45', transverse bores 46, 46' are introduced into the tube 12, through which the thermal adhesive 47, 47' in which the heat pipes 40, 40' are embedded (see FIG. 3) can escape during the mounting in the lengthwise bore 18. The distal end section of each heat pipe 40, 40' shown in FIG. 4 is thermally coupled to the tube 12 by the thermal adhesive 47, 47'. As is likewise shown in FIG. 4, the overhanging section 16 of the tube 12 forms the working space 15. Further, the lengthwise continuous slot 19 of the tube 12 can be seen at the distal end of the tube 12 (also see FIG. 3).

Figure 5:
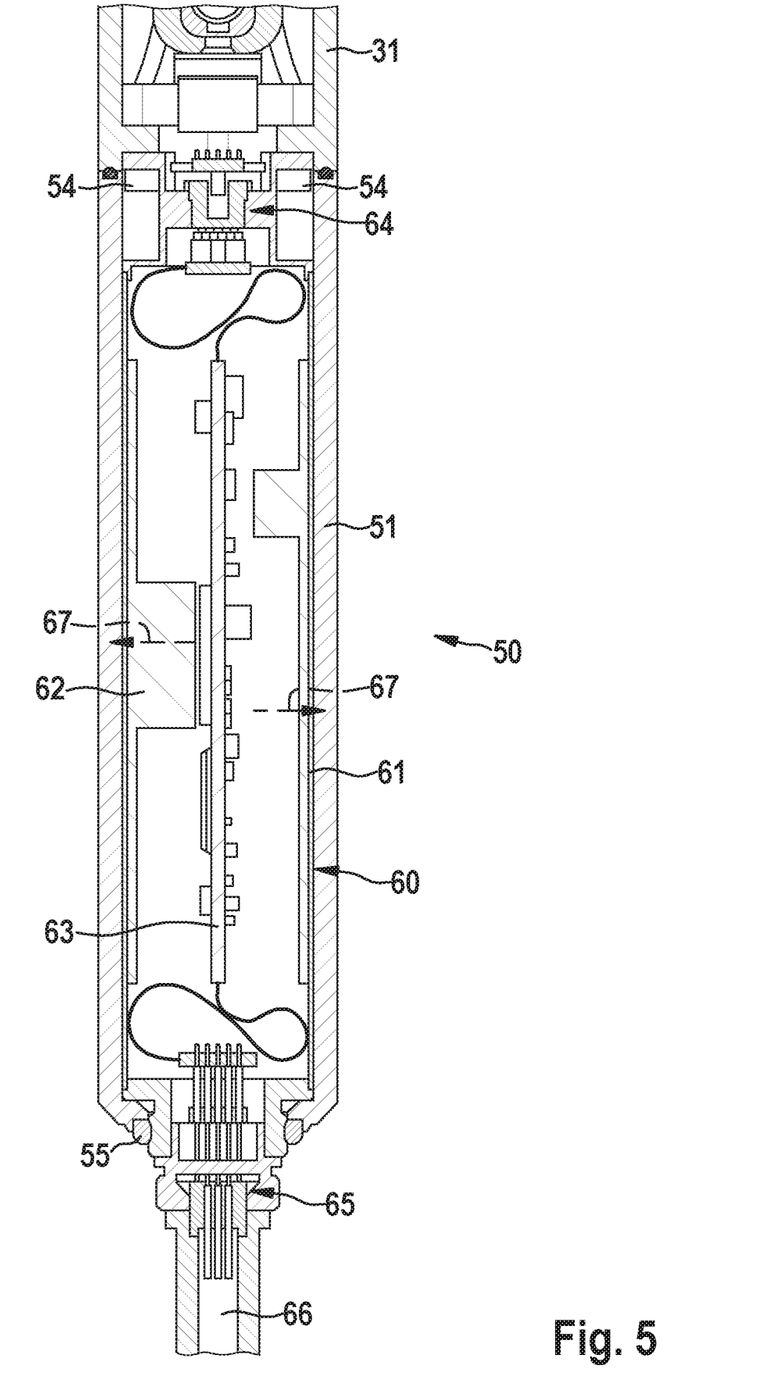
FIG. 5 shows a transverse section through the lower region of the handle of the endoscope of FIG. 1.

FIG. 5 shows the handle 50 cut open in the region of the housing 51, approximately as a continuation of the cross section shown in FIG. 3 at bottom. The housing 51 of the handle 50 holds the electronics unit 60, which has a metallic shell 61 in which is mounted an aluminum support 62 which carries the power supply board 63. The power supply board 63 has electronic circuits for the control of the LED 33, for the powering of the electronic image sensor 23, and for the image preprocessing of the signals provided by the electronic image sensor 23. For this, the power supply board 63 is connected by a connector 64 and the corresponding cables 28, 35 to the image sensor 23 and to the LED 33 (see FIG. 2). The cables 28, 35 may be formed for example as a flex board or as ribbon cables. Moreover, the power supply board 63 is connected via the connector 64 and the cables 57 to an array of buttons 53 which are installed in the housing 51 of the handle 50 and by means of which various functions of the mediastinoscope 1 can be controlled, such as the brightness of the illumination and an electronic zoom function. Furthermore, the power supply board 63 is connected via a connector 65 to connecting cables 66 serving for connection to an external power supply and evaluation device, which may also comprise in particular a monitor as well as further operator elements.

The aluminum support 62 is adapted to the outfitting of the power supply board 63 and has for example an adequate thickness to fill up most of the space between the shell 61 and the power supply board 63 in the areas in which most of the heat loss is produced during the operation of the power supply board 63. The power supply board 63, moreover, is thermally coupled by means of thermal paste or adhesive to the aluminum support 62, and the latter is in turn thermally coupled by means of thermal paste or adhesive to the shell 61. A space between the power supply board 63 and the shell 61 can also be filled up with thermal paste or adhesive. The shell 61 lies flush against the inside of the housing 51. In order to improve the thermal coupling of the electronics unit 60 to the housing 51, additional thermal paste can be used. The heat transport through the aluminum support 62 and thermal paste or adhesive into the housing is indicated by the arrows 67 in FIG. 5.

The electronics unit 60 is hermetically sealed, so that the connectors 64, 65 are installed hermetically tight in the metallic shell 61. As mentioned above, the optical shaft 20 together with the connector housing 26 is also hermetically tight. The mediastinoscope 1 is sealed off as a whole, for which the seal 52 is provided, for example. The mediastinoscope 1 can thus be easily cleaned and sterilized, without having to be disassembled, and it can be autoclaved as a whole, if designed accordingly. But since a penetration of moisture into the interior of the head piece housing 31 cannot be entirely prevented on account of the seals 52 and the properties of optical fibers, the LED 33 including the proximal end of the light guide 36 or the light guide socket 37 which is optically coupled to the LED 33 is encased in casting compound (not shown in the figures), in order to further seal off the LED 33 and protect it as much as possible against the penetration of moisture.

As indicated in FIG. 5, the electronics unit 60 is fastened by means of screws 54 to the head piece housing 31. However, the screws 54 are not accessible in the assembled state of the mediastinoscope 1. The housing 51 of the handle 50 is held by a cap nut 55 on the electronics unit 60. In order to replace the electronics unit 60, for example if it becomes damaged, the cap nut 55 will be loosened, for which a special tool is needed. The housing 51 of the handle 50 can then be pulled off from the shell 61 of the electronics unit 60, so that the screws 54 become accessible and can be loosened, while the cables 57 are long enough so that the connector 64 only has to be loosened after the shell has been pulled off. After loosening the connector 64, 65, the electronics unit 60 can then be removed and replaced. In this way, a replacement of the electronics unit 60 is made possible without having to replace the shaft 10 with the optical shaft 20 at the same time.

Further details of the hermetically tight design of the electronics unit 60 and the sealing and disassembly of the mediastinoscope 1 are described in the German patent application of the same applicant, filed on the same date as the present application, entitled "Video endoscope" (our reference: KST083), which is incorporated here in the present application by reference.

When the mediastinoscope 1 is placed in operation, heat loss is produced in the power supply board 63 and in the LED 33. The heat loss of the power supply board 63 is taken, as described above, through the aluminum support 62 and the shell 61 to the housing 51 of the handle 50, and the heat transport can be improved by thermal paste or thermal adhesive. The heat loss of the LED 33 is taken in a small portion via the carrier plate 34 and the support 38 to the head piece housing 31 and it is taken up in a larger portion by the heat pipes 40, 40' (see FIG. 3). The heat pipes 40, 40' transport the respective portion of the heat loss of the LED 33 in the distal direction to the shaft 10 of the mediastinoscope 1 and at least partly to the distal end section 14 of the shaft 10 (see FIG. 4). The portion of the heat loss transported there heats the tube 12 in the area of the distal end section 14 of the shaft 10 by the thermal adhesive 47, 47' in which the heat pipes 40, 40' are embedded in the blind bores 45, 45'. Since the optical shaft 20 is enclosed on all sides by the tube 12, the optical shaft 20 as well as the lens 22 and the cover glass 27 installed in the distal end of the optical shaft 22 are also heated. Even a slight heating of the cover glass 27 is enough to prevent a fogging of the cover glass 27 when the shaft 10 is introduced into an internal bodily cavity.

The heat loss of the power supply board 63 that is introduced into the housing 51 as well as the portion of the heat loss of the LED 33 that is introduced into the head piece housing 31 is given off substantially to the surroundings. The rest of the heat loss of the LED 33 is introduced via the heat pipes 40, 40' into the shaft 10 and likewise dissipated via the tube 12 to the surroundings or utilized to heat the cover glass 27. The electronic image sensor 23 likewise produces heat loss during its operation, but this is generally less than the heat loss given off by the LED 33. The arrow 48 in FIG. 4 symbolically shows a corresponding heat flux inside the heat pipe 40', which is generally oriented in the distal direction, depending on the temperature gradient and depending on the heat output of the electronic image sensor, but it may also be oriented in theory in the proximal direction. The flow of heat from the heat pipe 40' to the surface of the tube 12 of the shaft 10 is indicated by the arrow 49. As can be seen in FIG. 4, the heat transport within the tube 12 occurs substantially or at least partially transversely to the longitudinal direction of the tube 12.

Thanks to the heat management method according to the technology, it is possible to dissipate the heat loss, which is produced for the most part in the proximal region of the mediastinoscope, optimally over distal and proximal regions of the surface of the mediastinoscope, while avoiding in any case any injury to bodily tissue caused by heat during the procedure. At the same time, a portion of the heat loss can be utilized to heat the distal end section of the mediastinoscope, so that the cover glass can also be heated; in this way, it is possible to prevent a fogging of the cover glass, especially at the start of an OP. At the same time, the mediastinoscope is designed to make possible an easy handling, cleaning, and sterilization, for example by autoclaving.

For sake of clarity, not all reference symbols are presented in all the figures. Reference symbols not explained in one figure have the same meaning as in the other figures.

LIST OF REFERENCE NUMBERS

1 Mediastinoscope
10 Shaft
11 Proximal end section
12 Pipe
13 Cavity
14 Distal end section
15 Working space
16 Overhanging section
17 Bulge
18 Lengthwise bore
19 Slot
20 Optical shaft
21 Imaging unit
22 Lens
23 Image sensor
24 Flex board
25 Connector
26 Connector housing
27 Cover glass
28 Cables 30 Head piece
31 Head piece housing
32 Light source
33 LED
34 Carrier plate
35 Cables
36 Light guide
37 Light guide socket
38 Support
40, 40' Heat pipe
41 Arrow
42 Arrow
43 Arrow
44 Arrow
45, 45' Blind bore
46, 46' Transverse bore
47, 47' Thermal adhesive
48 Arrow
49 Arrow
50 Handle
51 Housing
52 Seal
53 Button
54 Screw
55 Cap nut
57 Cables
60 Electronics unit
61 Shell
62 Aluminum support
63 Power supply board
64 Connector
65 Connector
66 Connecting cables
67 Arrow

The invention claimed is:

1. An endoscope comprising:
an elongated shaft and a head piece situated at a proximal end section of the shaft, wherein a heat source is arranged in the head piece, wherein at least one heat pipe extends inside the shaft, wherein a proximal end section of the at least one heat pipe is thermally coupled to the heat source, and
an optical system which is closed by a cover glass arranged in a distal end section of the shaft, wherein:
the heat source is a light source configured to generate an illumination radiation,
the at least one heat pipe extending in the distal direction as far as the distal end section of the shaft,
at least one distal end section of the heat pipe is thermally coupled to the distal end section of the shaft and to an outer shaft configured to heat the cover glass, and
the at least one heat pipe is inserted into a blind bore of the elongated shaft extending in a longitudinal direction of the shaft, the blind bore is connected near a distal end thereof by a transverse bore to an additional lengthwise bore of the elongated shaft, and the at least one heat pipe is embedded in thermal adhesive in the blind bore.

2. The endoscope according to claim 1, wherein the optical system is received in an optical shaft, which extends in the shaft of the endoscope and whose distal end section is thermally coupled to the distal end section of the shaft.

3. The endoscope according to claim 1, wherein the at least one heat pipe is thermally coupled in a middle section to the shaft.

4. The endoscope according to claim 1, wherein the outer shaft includes a section extending in the distal direction beyond the cover glass, wherein the at least one heat pipe extends in the distal direction only as far as the cover glass or approximately as far as the cover glass.

5. The endoscope according to claim 1, wherein the additional lengthwise bore is a through bore, wherein the optical system is received in the through bore.

6. The endoscope according to claim 1, wherein the shaft comprises an outer shaft comprising the blind bore, the transverse bore and the additional lengthwise bore, wherein the outer shaft is formed as a single piece.

7. The endoscope according to claim 1, wherein the endoscope comprises two heat pipes arranged on either side of the optical system.

8. The endoscope according to claim 1, wherein the light source comprises at least one LED and a LED support, wherein the at least one heat pipe is thermally coupled to the LED support.

9. The endoscope according to claim 1, wherein the endoscope comprises a handle with a housing, wherein an electronics unit is received in the housing, having a shell which lies flush with or interlocking against an inside of the housing.

10. The endoscope according to claim 9, wherein the electronics unit comprises a board with a metallic support of the board, which is thermally coupled to the shell by a thermal paste and/or thermal adhesive.

11. The endoscope according to claim 1, wherein the endoscope is a mediastinoscope.

12. An endoscope comprising:
an elongated shaft;
a head piece located at a proximal end section of the shaft;
a heat source arranged in the head piece, wherein at least one heat pipe extends inside the shaft, and a proximal end section of the at least one heat pipe is thermally coupled to the heat source, wherein the heat source is a light source configured to generate illumination; and
an optical system, which is closed by a cover glass, is located at a distal end section of the shaft, wherein the at least one heat pipe extends in the distal direction as far as the distal end section of the shaft, and at least one distal end section of the heat pipe is thermally coupled to the distal end section of the shaft and to an outer shaft to heat the cover glass, wherein the at least one heat pipe is inserted into a blind bore of the elongated shaft extending in a longitudinal direction of the shaft, the blind bore is connected near a distal end thereof by a transverse bore to an additional lengthwise bore of the elongated shaft, and the at least one heat pipe is embedded in thermal adhesive in the blind bore.

* * * * *